United States Patent [19]

Wright, Jr.

[11] 3,947,408

[45] Mar. 30, 1976

[54] PYRROLO-BENZODIAZEPINES, METHOD OF PREPARATION AND METHOD OF USE

[75] Inventor: William Blythe Wright, Jr., Woodcliff Lake, N.J.

[73] Assignee: American Cyanamid Company, Stamford, Conn.

[22] Filed: Aug. 5, 1974

[21] Appl. No.: 494,657

[52] U.S. Cl. .... 260/239.3 T; 260/239.3 P; 424/274; 260/326.2; 260/340.5
[51] Int. Cl.² ...................................... C07D 487/04
[58] Field of Search ............... 260/239.3 T, 239.3 P

[56] References Cited
UNITED STATES PATENTS

| | | | |
|---|---|---|---|
| 3,324,116 | 6/1967 | Doebel et al. | 260/239.3 T |
| 3,483,187 | 12/1969 | Doebel et al. | 260/239.3 T |
| 3,732,212 | 5/1973 | Carabateas | 260/239.3 T |

*Primary Examiner*—John M. Ford
*Assistant Examiner*—Robert T. Bond
*Attorney, Agent, or Firm*—Denis A. Polyn

[57] ABSTRACT

Derivatives of 1,2,3,5,10,11a-hexahydro-11H-pyrrolo[2,1-c][1,4]benzodiazepin-11-one in the form of their racemic mixtures, optical isomers and salts, their method of preparation and method of use are described. The compounds are useful in treating anxiety in warm-blooded animals.

6 Claims, No Drawings

PYRROLO-BENZODIAZEPINES, METHOD OF PREPARATION AND METHOD OF USE

DESCRIPTION OF THE INVENTION

The invention relates to new racemic compounds, optical isomers, salts, method of preparation and method of use of 1,2,3,5,10,11a-hexahydro-11H-pyrrolo[2,1-c][1,4]benzodiazepin-11-ones.

The racemic compounds and optical isomers of the present invention may be illustrated by the following formula:

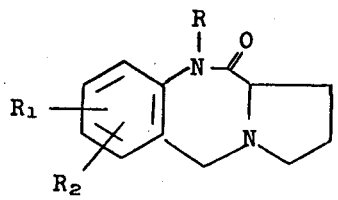

wherein R is lower alkyl, allyl, propargyl, trifluoroethyl, cycloalkylmethyl, hydroxyethyl, and lower alkoxyethyl. $R_1$ and $R_2$ are hydrogen, lower alkyl, chloro, fluoro, bromo, cyano, nitro, amino, trifluoromethyl, methoxy, and hydroxy, and $R_1$ and $R_2$ taken together on adjacent carbon atoms may be methylenedioxy and a pharmaceutically acceptable salt thereof. The term "lower alkyl" and lower alkoxy includes those having 1 to 4 carbon atoms and cycloalkyl those having 3 to 6 carbon atoms.

The free bases of the racemic compounds or optical isomers of this invention, in general, may be either liquids or solids at room temperature. The free bases are, in general, relatively insoluble in water, but soluble in most organic solvents such as lower alkyl alcohols, benzene, acetone, chloroform or the like. These compounds form acid addition salts with strong acids, such as hydrochloric acid, sulfuric acid, phosphoric acid, and the like. The compounds also form salts with organic acids, as for example, fumaric and maleic acid. These salts, in general, are soluble in water, methanol, and ethanol, but relatively insoluble in benzene, ether, petroleum ether and the like.

The compounds of this invention can be prepared by one of the following methods of which the first method has been found most advantageous.

FIRST METHOD

A derivative of 1,2,3,11a-tetrahydro-5H-pyrrolo[2,1-c][1,4]benzodiazepin-5,11(10H)-dione (prepared as described in my copending application, Ser. No. 464,424, filed Apr. 26, 1974) is treated with a solution of borane in tetrahydrofuran or other suitable solvent, and the derivative of 1,2,3,5,10,11a-hexahydro-11H-pyrrolo[2,1-c][1,4]benzodiazepin-11-one is recovered from the reaction mixture. The following equation describes the reaction which takes place:

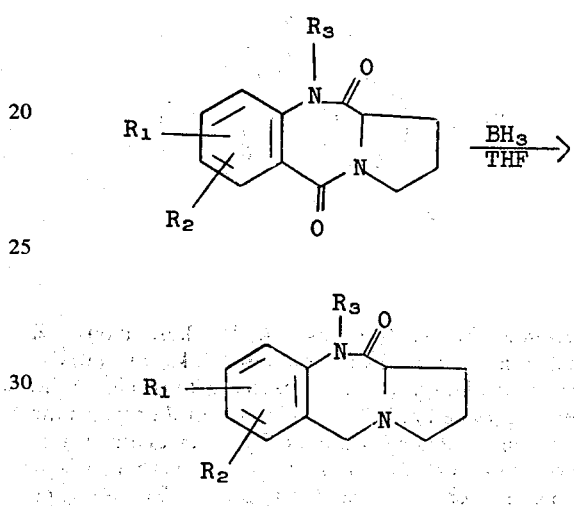

where $R_3$ is lower alkyl, trifluoroethyl, cycloalkylmethyl, hydroxyethyl, and lower alkoxyethyl, and $R_1$ and $R_2$ are as described hereinbefore.

The reaction is usually carried out at room temperature or at room temperature followed by a short period at reflux temperature.

SECOND METHOD

The following equations illustrate the second method:

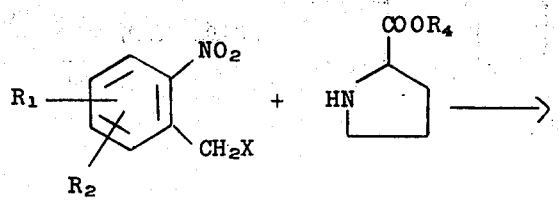

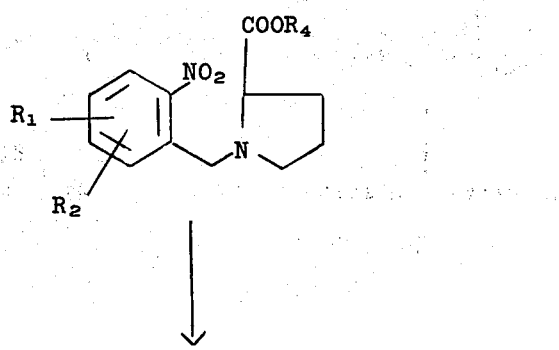

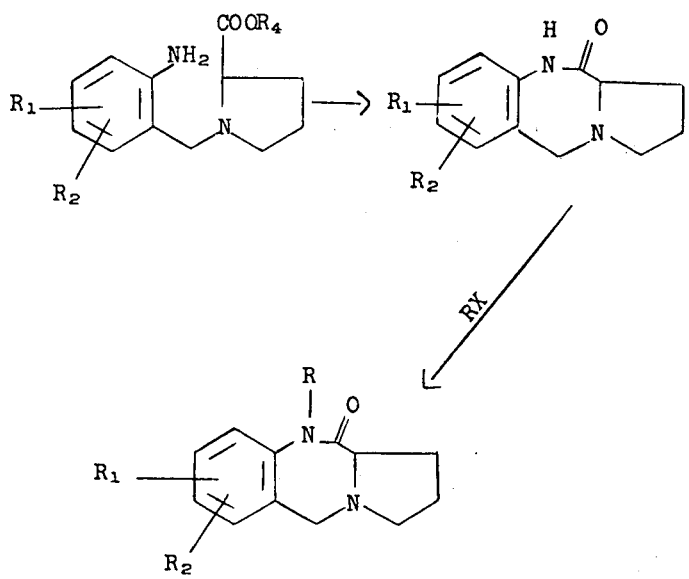

wherein R, $R_1$ and $R_2$ are as described hereinabove, X is halogen and $R_4$ is hydrogen, lower alkyl or benzyl.

An o-nitrobenzyl halide is treated with proline or an ester of proline and the resulting o-nitrobenzylproline derivative is reduced (chemically or catalytically) to the o-amino derivative and cyclized by heating as is or in the presence of acid or base. The resulting 1,2,3,5,10,11a-hexahydro-11H-pyrrolo[2,1-c][1,4]benzodiazepin-11-one (prepared by this or any other method) is alkylated, preferably in the presence of an alkaline catalyst such as sodium, sodium methylate or sodium hydride, to the desired compounds.

THIRD METHOD

A third method can be illustrated as follows:

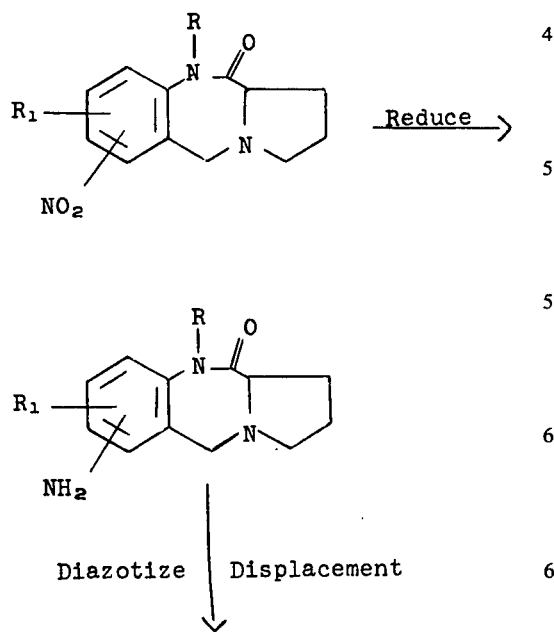

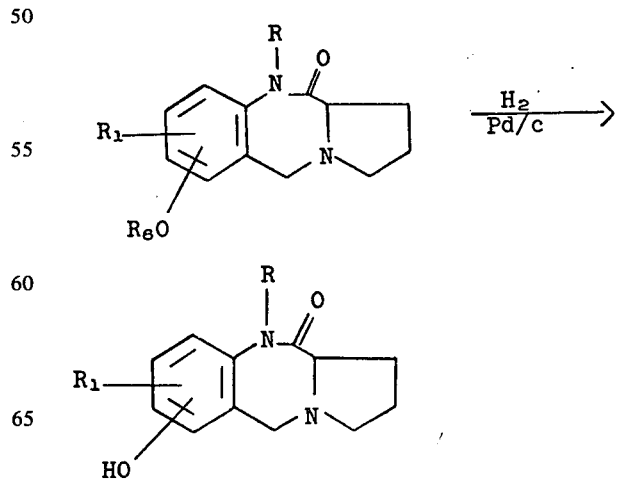

wherein R and $R_1$ are as hereinbefore defined and $R_5$ is hydroxyl, chloro, bromo, fluoro, methoxy or cyano.

A nitro substituted 1,2,3,5,10,11a-hexahydro-11H-pyrrolo[2,1-c][1,4]benzodiazepin-11-one is reduced catalytically or chemically to the amino derivative. This compound is then diazotized and decomposed to give the hydroxy derivative, or in the presence of cuprous salts to give the cyano or halo derivative (Sandmeyer Reaction) or in the presence of methanol to give the methoxy derivative.

FOURTH METHOD

This method can be illustrated as follows:

wherein R and $R_1$ are as defined hereinbefore and $R_6$ is benzyl.

A benzyloxy substituted 1,2,3,5,10,11a-hexahydro-11H-pyrrolo[2,1-c][1,4]benzodiazepin-11-one is hydrogenated in the presence of a catalyst such as palladium oxide or palladium-on-carbon to yield the corresponding hydroxy analog.

FIFTH METHOD

This method may be illustrated as follows:

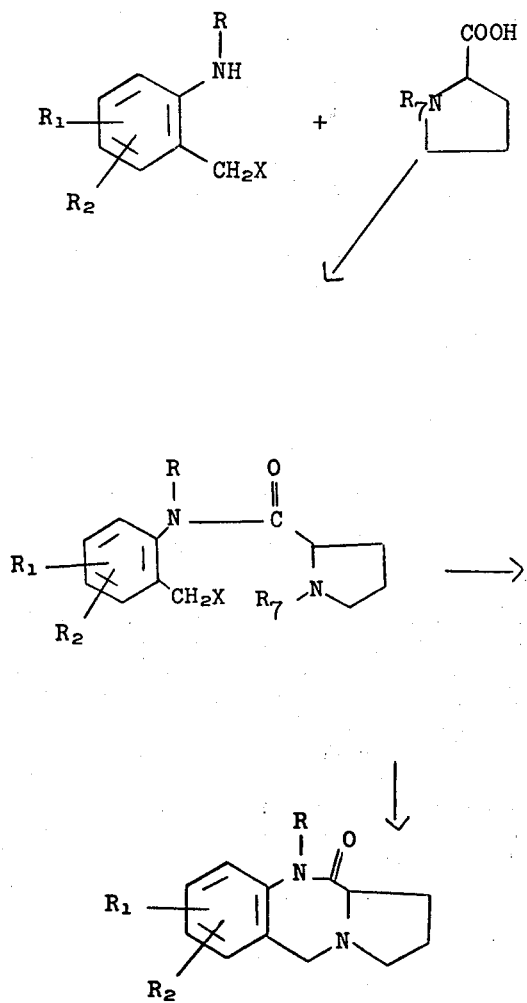

wherein R, $R_1$ and $R_2$ are as defined above, X is halogen or other displaceable group and $R_7$ is hydrogen or a group such as benzyl or carbobenzoxy which can be removed before cyclization.

In this method, an o-aminobenzyl halide is condensed with proline or an N-substituted proline derivative. Such reagents as thionyl chloride, phosphorus pentachloride, carboxyl diimidazole, dicyclohexylcarbodiimide are desirable condensing agents. The resulting amide is cyclized by heating alone or in a solvent (50°–200°C.) or is first freed of the $R_7$ substituent and then cyclized.

In carrying out the preparation of the present compounds, combinations of the above methods may be used.

The compounds of the present invention possess central nervous system activity at non-toxic doses, and as such, are useful as anxiolytic agents. The compounds have been tested pharmacologically and found to have properties which show a desirable wide spread between doses producing anxiolytic activity and toxic symptoms.

The anti-anxiety properties of the compounds of the present invention have been established in a test which indicates anxiolytic activity by a measure of protection from convulsions resulting from the administration of pentylenetetrazole. Graded dose levels of the compounds of this invention are administered orally, in a 2% starch vehicle, to groups of at least 5 rats. At the estimated time of peak effect, the rats are treated intravenously with pentylenetetrazole at a dose of 21 to 23 mg./kg. of body weight. This dose is estimated to cause clonic seizures in 99% of unprotected rats. The effective dose of the test compound for protection of 50% of the animals is calculated by the method of D. H. Finney in Statistical Methods in Biological Assay, Second Edition, Hafner Publishing Co., New York, 1964, pp. 456–457. Representative results are given in the table which follows in comparison with Librium (chlordiazepoxide) or Valium (diazepam), all of which were tested in exactly the same manner. It has been reported [R. T. Hill and D. H. Tedeschi, "Animal Testing and Screening Procedures in Evaluating Psychotropic Drugs" in An Introduction to Psychopharmacology, Eds. R. R. Rech and K. E. Moore, Raven Press, New York, pp. 237–288 (1971)] that there is a high degree of correlation between antagonism of pentylenetetrazole seizures in rats and antianxiety effects in higher warm-blooded animals.

TABLE I

| PROTECTION AGAINST CLONIC SEIZURES CAUSED BY PENTYLENETETRAZOLE IN RATS | |
|---|---|
| Compound | MEDIAN EFFECTIVE ORAL DOSE (mg./kg.) $ED_{50}$ |
| 1. Dextro 1,2,3,5,10,11a-hexahydro-10-methyl-11H-pyrrolo[2,1-c][1,4]-benzodiazepin-11-one hydrochloride | 15 |
| 2. Racemic 1,2,3,5,10,11a-hexahydro-10-methyl-11H-pyrrolo[2,1-c][1,4]benzodiazepin-11-one hydrochloride | 66 |
| 3. Dextro 7-chloro-1,2,3,5,10,11a-hexahydro-10-methyl-11H-pyrrolo[2,1-c][1,4]benzodiazepin-11-one hydrochloride | 80 |
| 4. Racemic 7-chloro-1,2,3,5,10,11a-hexahydro-10- | 91 |

TABLE I-continued

PROTECTION AGAINST CLONIC SEIZURES CAUSED BY PENTYLENETETRAZOLE IN RATS

| Compound | MEDIAN EFFECTIVE ORAL DOSE (mg./kg.) $ED_{50}$ |
|---|---|
| methyl-11H-pyrrolo[2,1-c][1,4]benzodiazepin-11-one hydrochloride | |
| 5. Dextro 7,10-dimethyl-1,2,3,5,10,11a-hexahydro-11H-pyrrolo[2,1-c][1,4]benzodiazepin-11-one hydrochloride | 32 |
| 6. Librium (chlordiazepoxide) | 2.5 |
| 7. Valium (diazepam) | 1.8 |

The compounds of the present invention may be administered to warm-blooded animals, in either their racemic or optical isomeric forms, orally, or parenterally if desired, and when so administered, may be considered as tranquilizing agents for therapeutically desirable treatment of anxiety in warm-blooded animals. The dosage regimen can be adjusted to provide optimum therapeutic response. Thus, for example, several doses may be administered daily, or the dose may be reduced proportionately as indicated by the requirements of the particular therapeutic situation.

For therapeutic administration the compounds of this invention may be incorporated with pharmaceutical carriers such as excipients and used, for example, in the form of tablets, dragees, capsules, liquids, elixirs, emulsions, suspensions, syrups, chocolate candy, wafers, chewing gum or the like for oral administration.

Parenteral solutions and suspensions may be prepared for intramuscular or subcutaneous administration, and suppositories may be prepared for rectal administration. Such compositions and preparations should contain at least 0.1% of active component. The percentage of the compositions and preparations may, of course, be varied, and may conveniently be between 2 and 60% or more of the weight of the unit. The amount of active component in such therapeutically useful compositions or preparations is such that a suitable dosage of from about 1.0 to about 25.0 mg./kg./day will be obtained. Preferred compositions or preparations according to the present invention are prepared so that a dosage unit form contains between about 20 and about 400 mg. of the therapeutically active component.

The compositions of this invention are physiologically active as anxiolytic agents. As such, they can be incorporated in various pharmaceutical forms such as set forth immediately above, for immediate or sustained release, by combining with suitable pharmaceutical carriers. They may be in the form of dosage units for a single therapeutic dose or in small units for multiple dosages or in larger units for division into single doses. Obviously, in addition to the therapeutic tranquilizing compound there may be present excipients, binders, fillers and other therapeutically inert ingredients necessary in the formulation of the desired pharmaceutical preparation.

SPECIFIC DISCLOSURE

The following specific examples illustrate the preparation of the racemic compounds and optical isomers of the present invention along with formulations of the active components.

EXAMPLE 1

Preparation of Dextrorotatory 1,2,3,5,10,11a-Hexahydro-10-methyl-11H-pyrrolo[2,1-c][1,4]benzodiazepin-11-one A mixture of 17.7 g. of N-methylisatoic anhydride, 12.3 g. of L-proline and 100 ml. of dimethylsulfoxide is heated on a steam bath for 6 hours, cooled and diluted with 300 ml. of water. The mixture is extracted with benzene to remove the desired product. The benzene layer is washed twice with water and concentrated to remove the solvent. The residue is triturated with ether. The crystals which form are collected by filtration and recrystallized from ethyl acetate yielding the pure (+)-1,2,3,11a-tetrahydro-10-methyl-5H-pyrrolo [2,1-c][1,4]benzodiazepin-5,11(10H)-dione, melting point 120°–122°C., $[\alpha]_D^{25}$ + 486° (1%, methanol).

A solution of 18.4 g. of (+)-1,2,3,11a-tetrahydro-10-methyl-5H-pyrrolo[2,1-c][1,4]benzodiazepin-5,11(10H)-dione (prepared immediately above) in 140 ml. of tetrahydrofuran is added dropwise over 5–10 minutes to 160 ml. of 1M borane in tetrahydrofuran. The reaction mixture is stirred at room temperature for one hour and then heated at reflux temperature for 1½ hours. The mixture is cooled and 45 ml. of 6N HCl is added dropwise. The solvent is distilled off at atmospheric pressure and the residue is cooled in an ice bath while adding 100 ml. of water and 33 g. of sodium hydroxide pellets. The desired product is extracted into benzene and the benzene layer is concentrated to recover the crude product. Further purification by partition chromatography on a diatomaceous earth column using a heptane/methyl cellosolve solvent system results in pure (+)-1,2,3,5,10,11a-hexahydro-10-methyl-11H-pyrrolo[2,1-c][1,4]benzodiazepin-11-one obtained as an oil, IR (C=O 6.02μ). This is treated with ether and ethanolic hydrochloric acid and the HCl salt, melting point 256°–258°C. $[\alpha]_D^{25}$ +415° (1.3% methanol) is obtained.

EXAMPLE 2

Preparation of Racemic 1,2,3,5,10,11a-Hexahydro-10-methyl-11 H-pyrrolo[2,1-c][1,4]benzodiazepin-11-one The above compound, melting point 80°–82°C., is obtained when racemic 1,2,3,11a-tetrahydro-10-methyl-52,1-c][1,4]benzodiazepin-5,11(10H)-dione (prepared from N-methylisotoic anhydride and DL-proline) is treated with borane in tetrahydrofuran as described in Example 1. The hydrochloride salt melts at 229°–231°C.

EXAMPLE 3

Preparation of levorotatory-1,2,3,5,10,11a-Hexahydro-10-methyl-11H-pyrrolo[2,1-c][1,4]benzodiazepin-11-one The above compound is obtained when (—)-1,2,3,11a-tetrahydro-10-methyl-5H-pyrrolo[2,1-c][1,4]benzodiazepin-5,11(10H)-dione, melting point 120-122°C. $[\alpha]_D 25$ —477°, (1.24%, methanol) and (prepared from N-methylisatoic anhydride and D-proline as described in Example 1) is treated with borane in tetrahydrofuran as described in Example 1.

EXAMPLE 4

Preparation of Dextrorotatory 10-Ethyl-1,2,3,5,10,11a-hexahydro-11H-pyrrolo[2,1-c][1,4]benzodiazepin-11-one When (+) 10-ethyl-1,2,3,11a-tetrahydro-5H-pyrrolo[2,1-c][1,4]benzodiazepin-5,11(10H)-dione, melting point 138°-140°C., (prepared as described above by reacting N-ethylisatoic anhydride with L-proline) is substituted for (+)-1,2,3,11a-tetrahydro-10-methyl-[5H-pyrrolo [2,1-c][1,4]benzodiazepin-5,11-(10H)-dione in the procedure of Example 1, the above compound is obtained. The hydrochloride salt melts at 233°-235°C., $[\alpha]_D^{25}$ + $^{415°}$ (0.9% in methanol).

EXAMPLE 5

Preparation of Racemic 7-Chloro-1,2,3,5,10,11a-hexahydro-10-methyl-11H-pyrrolo[2,1-c][1,4]benzodiazepin-11-one If 7-chloro-1,2,3,11a-tetrahydro-10-methyl-5H-pyrrolo[2,1-c][1,4]benzodiazepin-5,11(10H)-dione (prepared as described in Example 1 from DL-proline and 5-chloro-N-methylisatoic anhydride) is treated with 1M borane in tetrahydrofuran as described in Example 1, the above compound is obtained. The hydrochloride salt melts at 243°-245°C.

EXAMPLE 6

Preparation of Dextrorotatory 7-Chloro-1,2,3,5,10,11a-hexahydro-10-methyl-11H-pyrrolo[2,1-c][1,4]benzodiazepin-11-one The above compound is obtained when (+)-7-chloro-1,2,3,11a-tetrahydro-10-methyl-5H-pyrrolo[2,1-c][1,4]-benzodiazepin-5,11(10H)-dione (melting point 155°-157°C. is prepared from L-proline and 5-chloro-N-methylisatoic acid as described in Example 1) is treated with 1M borane in tetrahydrofuran as described in Example 1. The hydrochloride salt melts at 270°-272°C., $[\alpha]_D^{25}$ + 377° (1.03%) methanol).

EXAMPLE 7

Preparation of Dextrorotatory 7,10-Dimethyl-1,2,3,5,10,11a-hexahydro-11H-pyrrolo[2,1-c][1,4]benzodiazepin-11-one When (+)-7,10-dimethyl-1,2,3,11a-tetrahydro-5H-pyrrolo[2,1-c][1,4]benzodiazepin-5,11(10H)-dione (melting point 137°-139°C., prepared from L-proline and N,5-dimethylisatoic anhydride as described in Example 1) is treated with 1M borane in tetrahydrofuran as described in Example 1, the above compound, melting point 80°-82° is obtained. The hydrochloride salt melts at 213°-215°C.

EXAMPLE 8

Preparation of Dextrorotatory 8-Chloro-1,2,3,5,10,11a-hexahydro-10-methyl-11H-pyrrolo[2,1-c][1,4]benzodiazepin-11-one This compound is obtained when (+)-8-chloro-1,2,3,11a-tetrahydro-10-methyl-5H-pyrrolo[2,1-c][1,4]benzodiazepin-5,11(10H)-dione (melting point 191°-194°C. prepared from L-proline and 4-chloro-N-methylisatoic anhydride is described in Example 1) is substituted for (+) 1,2,3,11a-tetrahydro-10-methyl-5H-pyrrolo[2,1-c][1,4]benzodiazepin-5,11(10H)-dione in the process of Example 1.

EXAMPLE 9

Preparation of 7,9-Dichloro-1,2,3,5,10,11a-hexahydro-10-methyl-11H-pyrrolo-[2,1-c][1,4]benzodiazepin-11-one If 7,9-dichloro-1,2,3,11a-tetrahydro-10-methyl-5H-pyrrolo[2,1-c][1,4]benzodiazepin-5,11(10H)-dione (prepared by reaction of proline and 3,5-dichloro-N-methylisatoic anhydride as described in Example 1) is treated with borane as described in Example 1, the above compound is obtained.

EXAMPLE 10

Preparation of 7-Bromo-1,2,3,5,10,11a-hexahydro-10-methyl-11H-pyrrolo[2,1-c][1,4]benzodiazepin-11-one The above compound is prepared when 7-bromo-1,2,3,11a-tetrahydro-10-methyl-5H-pyrrolo[2,1-c][1,4]-benzodiazepin-5,11(10H)dione (prepared by reaction of proline and 5- bromo N-methylisatoic anhydride as described in Example 1) is treated with 1M borane in tetrahydrofuran as described in Example 1.

EXAMPLE 11

Preparation of 7-Fluoro-1,2,3,5,10,11a-hexahydro-10-methyl-11H-pyrrolo[2,1-c][1,4]benzodiazepin-11-one When 7-fluoro-1,2,3,11a-tetrahydro-10-methyl-5H-pyrrolo [2,1-c][1,4]benzodiazepin-5,11(10H)-dione (prepared from proline and 5-fluoro N-methylisatoic anhydride as described in Example 1) and borane are reacted as described in Example 1, the above compound is obtained.

EXAMPLE 12

Preparation of 1,2,3,5,10,11a-Hexahydro-10-methyl-7-trifluoromethyl-11H-pyrrolo[2,1-c][1,4]benzodiazepin-11-one If 1,2,3,11a-tetrahydro-10-methyl-7-trifluoromethyl-5H-pyrrolo[2,1-c][1,4]benzodiazepin-5,11(10H)-dione (prepared from proline and 5-trifluoromethyl N-methylisatoic anhydride as described in Example 1) is treated with 1M borane in tetrahydrofuran as described in Example 1, the above compound is obtained.

EXAMPLE 13

Preparation of 9-Chloro-1,2,3,5,10,11a-hexahydro-7-methoxy-10-methyl-11H-pyrrolo[2,1-c][1,4]benzodiazepin-11-one This compound is obtained when a mixture of 1M borane in tetrahydrofuran and 9-chloro-1,2,3,11a-tetrahydro-7-methoxy-10-methyl-5H-pyrrolo[2,1- c][1,4]benzodiazepin-5,11-(10H)-dione (prepared from proline and 3-chloro-5-methoxy-N-(methylisatoic anhydride as described in Example 1) are allowed to react as described in Example 1.

EXAMPLE 14

Preparation of
7,8-Dimethoxy11,2,3,5,10,11a-hexahydro-10-methyl-11H-pyrrolo [2,1 -c][1,4]benzodiazepin-11-one The above compound is prepared when 7,8-dimethoxy-1,2,3,11a-tetrahydro-10-methyl-5H-pyrrolo[2,1-c][1,4]benzodiazepin-5,11(10)-dione (prepared from proline and 4,5-dimethoxy-N-methylisatoic anhyride as described in Example 1) is treated with 1M borane in tetrahydrofuran as described in Example 1.

EXAMPLE 15

Preparation of
7,8-Methylenedioxy-1,2,3,5,10,11a-hexahydro-10-methyl-11H-pyrrolo2,1-c][1,4]benzodiazepin-11-one When 1M borane in tetrahydrofuran and 7,8-methylenedioxy-1,2,3,11a-tetrahydro-10-methyl-5H-pyrrolo[2,1-c][1,4]benzodiazepin-5,11(10H)-dione (prepared from proline and 4,5-methylenedioxy-N-methylisatoic anhydride by the procedure of Example 1) are allowed to react as described in Example 1, the above compound is obtained.

EXAMPLE 16

Preparation of 1,2,3,5,10,11a-Hexahydro-11H-pyrrolo [2,1-c][1,4]benzodiazepin-11-one The above compound, melting point 174°–176°c., is obtained when 1,2,3,11a-tetrahydro-5H-pyrrolo [2,1-c][1,4]benzodiazepin-5,11(10H)-dione (prepared from proline and isatoic anhydride by the procedure of Example 1) is treated with 1M borane in tetrahydrofuran as described in the procedure of Example 1.

EXAMPLE 17

Preparation of 1,2,3,5,10,11a-Hexahydro-11H-pyrrolo [2,1-c][1,4]benzodiazepin-11-one The above compound may also be prepared by the following procedure.

A solution of 17,1 g. of o-nitrobenzyl chloride in 80 ml. of toluene is added dropwise to a mixture of 16.0 g. of potassium carbonate, 14,3 g. of ethyl pyrrolidine-2-carboxylate and 80ml. of toluene. The reaction mixture is heated at reflux temperature for 10 hours, cooled and treated with an excess of dilute hydrochloric acid. The layers are separated and the toluene layer is extracted once more with 2N hydrochloric acid. The aqueous layers are washed once with toluene and then alkalized with sodium hydroxide to pH 10. The crude ethyl 1-(o-nitrobenzyl)pyrrolidine-2-carboxylate is extracted into chloroform and further purified by distillation under reduced pressure.

A solution of 18.9 g. of ethyl 1-(o-nitrobenzyl)- pyrrolidine-2-carboxylate in 250 ml. of ethanol is hydrogenated over Raney nickel at room temperature and atmospheric pressure. The catalyst is filtered off and the mother liquor concentrated to recover the ethyl 1-(o-aminobenzyl)pyrrolidine- 2-carboxylate.

A mixture of 17.4 g. of ethyl 1-(o-aminobenzyl)-pyrrolidine-2-carboxylate and 350 ml. of 3 N hydrochloric acid is heated at reflux temperature for 6 hours. The reaction mixture is cooled, 5 N sodium hydroxide is added to pH 10, and the crude product is extracted into methylene chloride. The extract is washed with water, dried over sodium sulfate and concentrated. The crude semi-crystalline residue is recrystallized from ethyl acetate or ethanol to recover pure 1,2,3,5,10,11a-hexahydro-11H-pyrrolo[2,1-c] [1,4]benzodiazepin-11-one, melting point 174°–176°C.

EXAMPLE 18

Preparation of
1,2,3,5,10,11a-Hexahydro-10-methyl-11H-pyrrolo-[2,1-c] [1,4]benzodiazepin-11-one A mixture of 10.1 g. of 1,2,3,5,10,11a-hexahydro-11H-pyrrolo[2,1-c] [1,4]benzodiazepin-11-one, 6.0 g. sodium methylate, and 200 ml. of ethanol is stirred at room temperature for 3 hours and 10 ml. of methyl iodide is added. Stirring is continued for 48 hours and the reaction mixture is concentrated under reduced pressure. The residue is treated with benzene and water and the layers are separated. The benzene layer is washed with water, dried over magnesium sulfate and concentrated. The residue is treated with ethanolic HCl and 1,2,3,5,10,11a-hexahydro-10-methyl-11H-pyrrolo[2,1-c]- [1,4]benzodiazepin-11-one hydrochloride is obtained. The melting point after recrystallization from ethanol and ether is 229°–231°C.

EXAMPLE 19

Preparation of
7-Chloro-1,2,3,5,10,11a-hexahydro-11H-pyrrolo-[2,1-c] [1,4]benzodiazepin-11-one The above compound, melting point 157-159°C., is obtained when 7-chloro-1,2,3,11a-tetrahydro-5H-pyrrolo[2,1-c]- [1,4]benzodiazepin-5,11(10H)-dione and 1 M borane in tetrahydrofuran are reacted by the procedure of Example 1.

EXAMPLE 20

Preparation of
7-Chloro-1,2,3,5,10,11a-hexahydro-10-methyl-11H-pyrrolo[2,1-c] [1,4]benzodiazepin-11-one This compound, melting point 97-99°C., is obtained when 7-chloro-1,2,3,5,10,11a-hexahydro-11H-pyrrolo[2,1-c] [1,4]- benzodiazepin-11-one is methylated as described in the procedure of Example 18.

EXAMPLE 21

Preparation of
1,2,3,5,10,11a-Hexahydro-10-trifluoroethyl-11H-pyrrolo[2,1-c] [1,4]benzodiazepin-11-one The above compound is obtained when 1,2,3,5,10,11a-hexahydro-2,1-c] [1,4]benzodiazepin-11-one and trifluoroethyliodide react as described in Example 18.

EXAMPLE 22

Preparation of
10-Butyl-1,2,3,5,10,11a-hexahydro-11H-pyrrolo-[2,1-c] [1,4]benzodiazepin-11-one When butylbromide is substituted for methyliodide in the procedure of Example 18, this compound is obtained.

EXAMPLE 23

Preparation of
10-Allyl-7-chloro-1,2,3,5,10,11a-hexahydro-
11H-pyrrolo[2,1-c] [1,4]benzodiazepin-11-one This compound is obtained when allyl bromide and 7-chloro-1,2,3,5,10,11a-hexahydro-11H-pyrrolo[2,1-c] [1,4]- benzodiazepin-11-one are allowed to react as described in Example 18.

EXAMPLE 24

Preparation of
1,2,3,5,10,11a-Hexahydro-10-propargyl-11H-
pyrrolo[2,1-c] [1,4]benzodiazepin-11-one When propargyl bromide is substituted for methyliodide in the procedure of Example 18, the above compound is obtained.

EXAMPLE 25

Preparation of
1,2,3,5,10,11a-Hexahydro-10-hydroxyethyl-11H-
pyrrolo[2,1-c][1,4]benzodiazepin-11-one This compound is obtained when 2-iodoethanol is substituted for methyliodide in the procedure of Example 18.

EXAMPLE 26

Preparation of
1,2,3,5,10,11a-Hexahydro-10-methoxyethyl-11H-
pyrrolo[2,1-c] [1,4]benzodiazepin-11-one When 2-methoxyethyl bromide is substituted for methyliodide in the procedure of Example 18, the above compound is obtained.

EXAMPLE 27

Preparation of
10-Cyclopropylmethyl-1,2,3,5,10,11a-hexahydro-
11H-pyrrolo[2,1-c] [1,4]benzodiazepin-11-one The above compound is obtained when methyliodide is replaced by cyclopropylmethylbromide in the procedure of Example 18.

EXAMPLE 28

Preparation of
7-Chloro-10-cyclobutylmethyl-1,2,3,5,10,11a-
hexahydro-11H-pyrrolo[2,1-c]
[1,4]benzodiazepin-11- one If 7-chloro-1,2,3,5,10,11a-hexahydro-11H-pyrrolo-[2,1-c] [1,4]benzodiazepin-11-one is treated with cyclobutylmethylbromide by the procedure of Example 18, the above product is obtained.

EXAMPLE 29

Preparation of
7-Benzyloxy-1,2,3,5,10,11a-hexahydro-10-methyl-
11H-pyrrolo[2,1-c] [1,4]benzodiazepin-11-one The above compound is obtained when 7-benzyloxy-1,2,3,11a-tetrahydro-10-methyl-5H-pyrrolo[2,1-c] [1,4]benzodiazepin- 5,11(10H)-dione (prepared from proline and 5-benzyloxy-N-methylisatoic anhydride by the procedure of Example 1) is treated with 1 M borane in tetrahydrofuran by the procedures of Example 1.

EXAMPLE 30

Preparation of
1,2,3,5,10,11a-Hexahydro-7-hydroxy-10-methyl-
11H-pyrrolo[2,1-c] [1,4]benzodiazepin-11-one A mixture of 6.44 g. of 7-benzyloxy-1,2,3,5,10,11a-hexahydro-10-methyl-11H-pyrrolo[2,1-c] [1,4]benzodiazepin-11- one, 200 ml. of ethanol and 1.0 g. of 10% palladium-on-carbon catalyst is shaken in a Parr hydrogenator under about 3 atmospheric of hydrogen pressure until the theoretical amount of hydrogen is absorbed. The catalyst is filtered off and the mother liquor is concentrated to remove the solvent. The residue is purified by partition chromatography on a diatomaceous earth column using a heptane/methyl cellosolve solvent system to yield pure 1,2,3,5,10,11a-hexahydro-7-hydroxy- 10-methyl-11H-pyrrolo[2,1-c] [1,4]benzodiazepin-11-one.

EXAMPLE 31

Preparation of
1,2,3,5,10,11a-Hexahydro-10-methyl-7-nitro-11H-
pyrrolo[2,1-c] [1,4]benzodiazepin-11-one This compound is obtained when 1,2,3,11a-tetrahydro- 10-methyl-7-nitro-11H-pyrrolo[2,1-c] [1,4]benzodiazepin-5,11- (10H]-dione (prepared from proline and 5-nitro-N-methylisatoic anhydride by the procedure of Example 1) is treated with 1 M borane in tetrahydrofuran by the procedure of Example 1.

EXAMPLE 32

Preparation of
7-Amino-1,2,3,5,10,11a-hexahydro-10-methyl-11H-
pyrrolo[2,1-c] [1,4]benzodiazepin-11-one A mixture of 5.0 g. of 1,2,3,5,10,11a-hexahydro-10-methyl-7-nitro-11H-pyrrolo[2,1-c] [1,4]benzodiazepin-11-one, 200 ml. of ethanol and 1.0 g. of 10% palladium-on-carbon catalyst is shaken in a Parr hydrogenator under about 3 atmospheres of hydrogen pressure until the theoretical amount of hydrogen is absorbed. The catalyst is filtered off and the mother liquor is concentrated to remove the solvent. The residue is purified by partition chromatography on a diatomaceous earth column using a heptane/methyl cellosolve solvent system to yield pure 7 -amino-1,2,3,5,10,11a-hexahydro-10-methyl-11H-pyrrolo[2,1-c]- [1,4]benzodiazepin-11-one.

EXAMPLE 33

Preparation of
1,2,3,5,10,11a-Hexahydro-7-hydroxy-10-methyl-
11H-pyrrolo[2,1-c] [1,4]benzodiazepin-11-one A solution of 3.5 g. of sodium nitrite in 30 ml. of water is added over a 30 minute period at 90°–95°C. to a rapidly stirred solution of 11.5 g. of 7-amino-1,2,3,5,10,11a- hexahydro-10-methyl-11H-pyrrolo[2,1-c] [1,4]benzodiazepin-11- one in 600 ml. of 0.05N hydrochloric acid. The solution is held at this temperature for 20 minutes longer, cooled, treated with an excess of sodium carbonate and the crude product is extracted into benzene. The benzene solution is concentrated to remove the solvent and the residue is purified by partition chromatography in order to obtain the pure 1,2,3,5,10,11a- hexahydro-7-hydroxy-10-methyl-11H-pyrrolo[2,1-c] [1,4]benzodiazepin- 11-one.

EXAMPLE 34

Preparation of
7-Bromo-1,2,3,5,10,11a-Hexahydro-10-methyl-11H-pyrrolo[2,1-c] [1,4]benzodiazepin-11-one.

A solution of 3.9 g. of sodium nitrate in 30 ml. of water is added with stirring over a 5 minute period to a cooled (−5° to 0°C.) mixture of 11.9 g. of 7-amino-1,2,3,5,10,11a-hexahydro-10-methyl-11H-pyrrolo[2,1c] [1,4]benzodiazepin- 11-one, 200 ml. of water and 25 ml. of 40% hydrobromic acid. The reaction mixture is held at this temperature for ten more minutes and then poured into a cold mixture of 8.8 g. of cuprous bromide, 35 ml. of 40% hydrobromic acid and 20 ml. of water. After 19 hours, hydrogen sulfide is passed in and the dark precipitate is filtered off. The filtrate is treated with activated carbon and carefully alkalized with sodium carbonate. The mixture is extracted with benzene and the benzene solution is washed with water and concentrated. The residue is purified by partition chromatography in order to obtain pure 7-bromo-1,2,3,5,10,11a-hexahydro-10-methyl-11H-pyrrolo[ 2,1-c] [1,4]benzodiazepin-11-one.

EXAMPLE 35

Preparation of
7-Chloro-1,2,3,5,10,11a-Hexahydro-10-methyl-11H-pyrrolo[2,1-c] [1,4]benzodiazepin-11- one A solution of 3,9 g. of sodium nitrite in 30 ml. of water is added over 10 minutes with stirring to a cooled (−10°to 0°C.) mixture of 11.5 g. of 7-amino-1,2,3,5,10,11a-    hexahydro-10-methyl-11H-pyrrolo[2,1-c] [1,4]benzodiazepin-11- one, 13 g. of $CuSO_4 \cdot 5H_2O$, 60 ml. of concentrated hydrochloric acid and 40 ml. of water. The mixture is stirred for one hour without cooling, poured into 80 ml. of concentrated ammonium hydroxide and extracted with benzene. The benzene layer is washed with water and concentrated to remove the solvent. The residue is purified by partition chromatography in order to obtain the pure 7-chloro-1,2,3,5,10,11a-hexahydro- 10-methyl-11H-pyrrolo[2,1-c] [1,4]benzodiazepin-11-one, which melts at 97°–99°C. The hydrochloride salt melts at 244°–246°C.

EXAMPLE 36

Preparation of
1,2,3,5,10,11a-Hexahydro-7-methoxy-10-methyl-11H-pyrrolo[2,1-c] [1,4]benzodiazepin-11-one A solution of 3.5 g. of sodium nitrite in 30 ml. of water is added over 1 hour at 48°–50°C. to a solution of 11.5 g. of 7-amino-1,2,3,5,10,11a-hexahydro-10-methyl-11H- pyrrolo[2,1-c] [1,4]benzodiazepin-11-one in 20 ml. of concentrated hydrochloric acid and 500 ml. of methanol. The reaction mixture is held at this temperature for 1 hour longer, diluted with an equal volume of water, neutralized with sodium carbonate and concentrated under reduced pressure to remove the methanol. The aqueous residue is extracted with benzene and the benzene layer is concentrated to remove the crude 1,2,3,5,10,11a-hexahydro-7-methoxy-10-methyl-11H- pyrrolo[2,1-c] [1,4]benzodiazepin-11-one. Further purification is by partition chromatography on a diatomaceous earth column using a heptane/methyl cellosolve solvent system.

EXAMPLE 37

Preparation of
7-Cyano-1,2,3,5,10,11a-hexahydro-10-methyl-11H-pyrrolo[2,1-c] [1,4]benzodiazepin-11-one A mixture of 28.0 g. of 7-amino-1,2,3,5,10,11a-hexahydro- 10-methyl-11-pyrrolo[2,1-c] `1,4]benzodiazepin-11-one, 25 ml. of 28% hydrochloric acid and 100 g. of cracked ice is stirred and a solution of 7.0 g. of sodium nitrite in 20 ml. of water is added over about 15 minutes with stirring. Ice is added as necessary to keep the temperature at 0°–5°. The mixture is neutralized (litmus paper) by adding of dry sodium carbonate and again cooled to 0.5°C. A solution of cuprous cyanide (prepared by adding 16.3 g. of sodium cyanide in 25 ml. of water to a suspension of 12.5 g. of cuprous chloride in 50 ml. of cold water) is cooled to 0°–9°C. by addition of ice and 25 ml. of benzene is poured on the surface. This mixture is vigorously stirred and the cold diazonium solution is added over about 30 minutes while maintaining the temperature at 0°–5°C. during the addition and for an additional 30 minutes. The temperature is allowed to rise over 3 hours to room temperature and then slowly warmed to 50°C. The mixture is again cooled, extracted with benzene. The benzene extracts are washed with water and concentrated to remove the solvent. The residue is purified by partition chromatography on a diatomaceous earth column using a heptane/methyl/cellosolve solvent system in order to obtain the pure 7-cyano-1,2,3,5,10,11a-hexahydro-10-methyl-11H-pyrrolo[2,1-c] [1,4]benzodiazepin- 11-one.

EXAMPLE 38

Preparation of
1,2,3,5,10,11a-Hexahydro-10-methyl-11H-pyrrolo-[2,1-c] [1,4]benzodiazepin-11-one A mixture of 2.5 g. of N-carbobenzoxyproline, 1.7 g. of N,N'-carbonyldiimidazole and 25 ml. of tetrahydrofuran is stirred for 1 hour at room temperature and 2.2 g. of o-(benzyloxymethyl)-N-methylaniline is added. The mixture is heated at reflux temperature for 4 hours and concentrated to remove the solvent. The residue is mixed with 200 ml. of ethanol and 2 g. of 10% palladium-on-carbon catalyst and shaken in a Parr hydrogenator under about 3 atmospheres of hydrogen pressure until uptake is complete. The catalyst is filtered off and the mother liquor is concentrated to remove volatile materials. The residue is extracted into methylene chloride. This solution is washed twice with water, dried over magnesium sulfate, and heated at reflux temperature for 6 hours with 5 ml. of thionyl chloride. The reaction mixture is washed twice with sodium carbonate solution, once with water and concentrated. The residue is purified by partition chromatography on a diatomaceous earth column using a heptane/ methyl cellosolve solvent system and 1,2,3,5,10,11a-hexahydro- 10-methyl-11H-pyrrolo[2,1-c] [1,4]benzodiazepin-11-one is obtained.

EXAMPLE 39

The following formulation can be used for administering the compounds of this invention as a tablet.

|  | Grams |
|---|---|
| dextro-1,2,3,5,10,11a-hexahydro-10-methyl-11H-pyrrolo[2,1-c][1,4]-benzodiazepin-11-one hydrochloride | 150.0 |
| Talc | 150.0 |
| Magnesium stearate | 5.0 |

The ingredients are mixed, screened and tableted to give 1000 tablets containing 150 mg. each of the therapeutic agent.

I claim:

1. A racemic benzodiazepine or an optical isomer thereof of the formula:

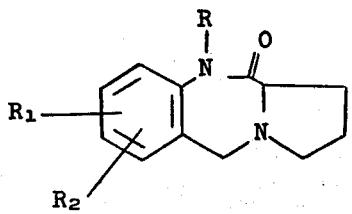

wherein R is lower alkyl, allyl, propargyl, trifluoroethyl, cycloalkylmethyl, hydroxyethyl and lower alkoxyethyl; $R_1$ and $R_2$ are hydrogen, lower alkyl, chloro, fluoro, bromo, cyano, nitro, amino, trifluoromethyl, methoxy, hydroxy and $R_1$ and $R_2$ taken together on adjacent carbon atoms is methylenedioxy and a pharmaceutically acceptable salt thereof.

2. The benzodiazepine in accordance with Claim 1, dextro 1,2,3,5,10,11a-hexahydro-10-methyl-11H-pyrrolo[2,1-c][1,4]benzodiazepin-11-one hydrochloride.

3. The benzodiazepine in accordanace with claim 1, racemic 1,2,3,5,10,11a-hexahydro-10-methyl-11H-pyrrolo[2,1-c]-[1,4]benzodiazepin-11-one hydrochloride.

4. The benzodiazepine in accordance with Claim 1, dextro 7-chloro-1,2,3,5,10,11a-hexahydro-10-methyl-11H-pyrrolo[2,1-c] [1,4-benzodiazepin-11-one hydrochloride.

5. The benzodiazepine in accordance with Claim 1, racemic 7-chloro-1,2,3,5,10,11a-hexahydro-10-methyl-11H-pyrrolo-[2,1-c] [1,4]benzodiazepin-11-one hydrochloride.

6. The benzodiazepine in accordance with Claim 1, dextro 7,10-dimethyl-1,2,3,5,10,11a-hexahydro-11H-pyrrolo[2,1-c][1,4]-benzodiazepin-11-one.

* * * * *